(12) United States Patent
Whitaker et al.

(10) Patent No.: US 7,429,245 B2
(45) Date of Patent: Sep. 30, 2008

(54) MOTION MANAGEMENT IN A FAST BLOOD PRESSURE MEASUREMENT DEVICE

(75) Inventors: Ty Whitaker, Arden, NC (US); Stephen C. Wilson, East Syracuse, NY (US); Knut Spang, Camillus, NY (US); Thaddeus J. Wawro, Auburn, NY (US); John A. Lane, Weedsport, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 757 days.

(21) Appl. No.: 10/619,380

(22) Filed: Jul. 14, 2003

(65) Prior Publication Data
US 2005/0033188 A1 Feb. 10, 2005

(51) Int. Cl.
*A61B 5/00* (2006.01)

(52) U.S. Cl. ................................. 600/494; 600/490

(58) Field of Classification Search .................. None
See application file for complete search history.

(56) References Cited

U.S. PATENT DOCUMENTS

| | | | |
|---|---|---|---|
| 4,262,674 A | 4/1981 | Uemura et al. | |
| 4,356,827 A | 11/1982 | Uemura et al. | |
| 4,461,266 A | 7/1984 | Hood, Jr. et al. | |
| 4,592,365 A * | 6/1986 | Georgi | 600/493 |
| 4,729,381 A | 3/1988 | Harada et al. | |
| 4,870,973 A * | 10/1989 | Ueno | 600/493 |
| 4,901,733 A | 2/1990 | Kaida et al. | |
| 4,928,700 A | 5/1990 | Harada | |
| 4,928,701 A | 5/1990 | Harada et al. | |
| 4,947,855 A | 8/1990 | Yokoe | |
| 4,951,679 A | 8/1990 | Harada | |
| 4,953,557 A | 9/1990 | Frankenreiter et al. | |
| 4,976,268 A | 12/1990 | Kurosawa | |
| 5,101,829 A | 4/1992 | Fujikawa et al. | |
| 5,131,400 A | 7/1992 | Harada et al. | |
| 5,135,003 A | 8/1992 | Souma | |

(Continued)

FOREIGN PATENT DOCUMENTS

DE 39 41 777 A1 12/1989

(Continued)

OTHER PUBLICATIONS

International Search Report dated Mar. 2, 2005.

*Primary Examiner*—Robert L Nasser
(74) *Attorney, Agent, or Firm*—Joseph B. Milstein; Hiscock & Barclay, LLP

(57) ABSTRACT

The invention is in one embodiment an apparatus and a method for measuring the blood pressure of a vertebrate subject. The apparatus uses an inflatable chamber with a sensor to detect signals indicative of a blood pressure of the subject during an inflation interval of the inflatable chamber. If secondary motion or artifact signals are detected, the apparatus and method determine whether the secondary signals are below a predetermined value, and if so, complete the measurement. If the signals indicate that the measurement is not accurate, the system and method immediately institute a measurement of the blood pressure during a deflation interval, which can include a step deflation interval. In the event that the subject is identified as a neonate, the system and method immediately measure using the deflation interval procedure.

20 Claims, 2 Drawing Sheets

U.S. PATENT DOCUMENTS

| | | | |
|---|---|---|---|
| 5,144,956 A | 9/1992 | Souma | |
| 5,179,956 A | 1/1993 | Harada et al. | |
| 5,335,665 A | 8/1994 | Suzuki | |
| 5,447,161 A | 9/1995 | Blazek et al. | |
| 5,462,051 A | 10/1995 | Oka et al. | |
| 5,560,366 A | 10/1996 | Harada et al. | |
| 5,595,180 A | 1/1997 | Ogura et al. | |
| 5,617,868 A | 4/1997 | Harada et al. | |
| 5,653,241 A | 8/1997 | Harada et al. | |
| 5,660,182 A | 8/1997 | Kuroshaki et al. | |
| 5,730,139 A | 3/1998 | Miyazaki et al. | |
| 5,759,157 A * | 6/1998 | Harada et al. | 600/494 |
| 6,068,601 A | 5/2000 | Miyazaki et al. | |
| 6,165,131 A * | 12/2000 | Cuce' et al. | 600/495 |
| 6,228,035 B1 * | 5/2001 | Packman et al. | 600/485 |
| 6,405,076 B1 * | 6/2002 | Taylor et al. | 600/513 |
| RE37,852 E | 9/2002 | Aso et al. | |
| 6,475,155 B2 | 11/2002 | Ogura et al. | |
| 6,511,435 B1 | 1/2003 | Bluth et al. | |
| 6,514,211 B1 | 2/2003 | Baura | |
| 6,517,495 B1 | 2/2003 | Hersh | |
| 6,519,486 B1 | 2/2003 | Edgar et al. | |
| 6,524,257 B2 * | 2/2003 | Ogura | 600/490 |
| 6,527,725 B1 | 3/2003 | Inukai et al. | |
| 6,554,773 B1 | 4/2003 | Nissila et al. | |
| 6,584,854 B2 | 7/2003 | Kimura et al. | |
| 6,589,186 B2 | 7/2003 | Nishibayashi | |
| 6,599,251 B2 | 7/2003 | Chen et al. | |
| 6,602,199 B2 | 8/2003 | Chen et al. | |
| 6,602,200 B1 | 8/2003 | Kubo et al. | |
| 6,607,492 B2 | 8/2003 | Ogura | |
| 6,610,017 B2 * | 8/2003 | Oka | 600/485 |
| 6,616,597 B2 | 9/2003 | Schock et al. | |
| 6,631,281 B1 | 10/2003 | Kastle | |
| 6,632,181 B2 | 10/2003 | Flaherty et al. | |
| 6,645,155 B2 | 11/2003 | Inukai et al. | |
| 6,648,828 B2 | 11/2003 | Friedman | |
| 6,654,623 B1 | 11/2003 | Kastle | |
| 6,689,069 B2 | 2/2004 | Bratteli et al. | |
| 6,699,195 B2 | 3/2004 | Nakazawa et al. | |
| 6,719,703 B2 | 4/2004 | Chen et al. | |
| 6,730,040 B2 | 5/2004 | Lee et al. | |
| 6,733,460 B2 * | 5/2004 | Ogura | 600/490 |
| 6,748,262 B2 | 6/2004 | Harada et al. | |
| 2003/0045801 A1 | 3/2003 | Chen et al. | |
| 2003/0092976 A1 | 5/2003 | Murase et al. | |
| 2003/0149371 A1 | 8/2003 | Shiga et al. | |
| 2003/0181816 A1 | 9/2003 | Shirasaki | |
| 2003/0187361 A1 | 10/2003 | Su | |
| 2003/0190062 A1 | 10/2003 | Noro et al. | |
| 2003/0199770 A1 | 10/2003 | Chen | |
| 2004/0002659 A1 | 1/2004 | Ohama | |
| 2004/0010198 A1 | 1/2004 | Yamakoshi et al. | |
| 2004/0034308 A1 | 2/2004 | Inoue et al. | |
| 2004/0054362 A1 | 3/2004 | Adams et al. | |

FOREIGN PATENT DOCUMENTS

| | | |
|---|---|---|
| EP | 0 684 101 A1 | 5/1995 |
| EP | 0 775 465 A1 | 5/1996 |
| EP | 1410757 | 4/2004 |
| EP | 1491136 A1 | 12/2004 |

* cited by examiner ofall ages, that are fast and are comfortable in use, and that provide for inadvertent motion by the subject patient.

MOTION MANAGEMENT IN A FAST BLOOD PRESSURE MEASUREMENT DEVICE

FIELD OF THE INVENTION

The invention relates to blood pressure measurement devices in general and particularly to devices that monitor the motion of the test subject.

BACKGROUND OF THE INVENTION

The traditional system and method for measuring blood pressure in vertebrate subjects such as human beings involves controlling the flow of blood in an extremity to cause circulation to stop, and noting pressures corresponding to the presence of audible sounds that occur as the blood circulation is allowed to resume. The method commonly includes applying an inflatable cuff to an extremity of the subject, pressurizing the inflatable cuff with a working fluid such as air to apply sufficient pressure to cause cessation of circulation in the extremity, and listening with a device such as a stethoscope while allowing the pressure applied to the extremity to decrease so as to identify a systolic blood pressure corresponding to the beginning of blood flow, and a diastolic blood pressure corresponding to the unrestricted flow of blood in the extremity. Characteristic sounds are heard upon the initial resumption of blood flow, which sounds end when the blood flow becomes unrestricted. Pressure is commonly measured in millimeters of mercury (mm. Hg) using a gauge such as a sphygmomanometer. U.S. Pat. No. 5,704,362, issued Jan. 6, 1998 to Hersh et al., describes older systems that employ Korotkoff sounds, as well as systems that use the oscillometric technique. One common problem is the discomfort associated with the elevated pressure that is applied with such systems.

Newer systems involve electronic sensors for measuring pressure within the inflatable cuff, and electronic sensors to detect the oscillatory pressures that occur within the inflatable cuff, and electronic sensors to detect the oscillatory pressures that occur within the cuff as a consequence of the pulsatile displacement of blood within the extremity. For example, U.S. Pat. No. 3,903,872, issued on Sep. 9, 1975 to Link, describes a system and method for measuring the oscillatory blood pressure using a cuff applied to an arm of a patient, and sensing sphygmometric information electronically. U.S. Patent Application Publication No. 2003/0069507 A1, by Nishibyashi, describes a cuff applied to a leg of a patient, also using electronic sensing apparatus to obtain non-invasive blood pressure information. U.S. Pat. No. 4,860,759, issued Aug. 29, 1989 to Kahn et al., describes an apparatus that measures blood pressure signals using an inflatable cuff and associated sensor equipment, and that processes the blood pressure information in conjunction with other sensed information, such as a pulse signal recorded from a finger probe. U.S. Pat. No. 5,704,362 describes mathematical analysis methods for extracting blood pressure information by fitting curves to blood pressure signals. The entire disclosure of each of the above identified patents and published applications is incorporated herein by reference in its entirety.

A number of problems in addition to discomfort have been observed with systems involving electronic sensors. Some of the problems include the inability to make accurate measurements in the presence of motion in the subject extremity, and the inability to make accurate measurements on very young patients.

There is a need for blood pressure measurement systems and methods that provide accurate measurements for patients

SUMMARY OF THE INVENTION

In one aspect, the invention relates to a blood pressure measurement apparatus. The apparatus comprises an inflatable chamber. The inflatable chamber is operable to be inflated during an inflation interval and deflated during a deflation interval. The apparatus includes a sensor coupled to the inflatable chamber, the sensor configured to measure a signal, the signal comprising information indicative of a blood pressure of a vertebrate. The apparatus includes a control module configured to receive as input at least a portion of the signal from the sensor, and to generate as output a control signal having a selected one of a plurality of values responsive to the input. The apparatus includes a first analysis module, the first analysis module configured to analyze the signal before the inflatable chamber is fully inflated to extract from the signal the blood pressure of the vertebrate. Furthermore, the apparatus includes a second analysis module, the second analysis module selectively operative in response to one of the plurality of values of the control signal, the second analysis module configured to analyze the signal during the deflation interval of the inflatable chamber to extract from the signal the blood pressure of the vertebrate, whereby the apparatus completes the measurement of the blood pressure of the vertebrate using at least one of the first analysis module and the second analysis module.

In one embodiment, the deflation interval comprises at least one step deflation interval. In one embodiment, the plurality of control signal values comprises a first value that inhibits operation of the second analysis module and a second value that activates operation of the second analysis module. In one embodiment, the blood pressure of the vertebrate comprises at least one of a systolic blood pressure and a diastolic blood pressure.

In one embodiment, the apparatus further comprises a reporting module configured to report at least one of the systolic blood pressure and the diastolic blood pressure.

In one embodiment, the apparatus further comprises a neonate sensor module configured to sense whether the vertebrate is a neonate vertebrate. In one embodiment, in response to a positive determination that the vertebrate is a neonate vertebrate, the apparatus completes a blood pressure measurement of the neonate vertebrate using the second analysis module. In one embodiment, the signal analyzed by the second analysis module during the deflation interval comprises a signal occurring during at least one step deflation interval. In one embodiment, the blood pressure of the neonate vertebrate comprises at least one of a systolic blood pressure and a diastolic blood pressure. In one embodiment, the apparatus further comprises a reporting module configured to report at least one of the systolic blood pressure and the diastolic blood pressure.

In another aspect, the invention features a blood pressure measurement apparatus. The apparatus comprises an inflatable chamber, the inflatable chamber operable to be inflated during an inflation interval and deflated during a deflation interval. The apparatus includes a sensor coupled to the inflatable chamber, the sensor configured to measure a signal, the signal comprising information indicative of a blood pressure of a vertebrate. The apparatus includes a first analysis module, the first analysis module configured to analyze the signal before the inflatable chamber is fully inflated to extract from the signal the blood pressure of the vertebrate. The apparatus includes a motion detection module configured to receive as input at least a portion of the signal from the sensor, the motion detection module configured to detect a secondary motion of the vertebrate distinct from motion associated with the signal comprising information indicative of a blood pressure of a vertebrate and configured to communicate a value to the first analysis module, whereby, in the event that the value of the secondary motion detected by the detection module is below a predetermined value, the apparatus completes a blood pressure measurement of the vertebrate using the first analysis module.

In one embodiment, the blood pressure of the vertebrate comprises at least one of a systolic blood pressure and a diastolic blood pressure. In one embodiment, the apparatus further comprises a reporting module configured to report at least one of the systolic blood pressure and the diastolic blood pressure. In one embodiment, the motion detection module is configured to provide a warning, the warning being generated in response to the secondary motion that exceeds the predetermined value.

In one embodiment, the apparatus further comprises an announcement module that announces the warning. In one embodiment, the announcement is a visual or an audible announcement, or both. In one embodiment, the blood pressure measurement is completed if the secondary motion falls below the predetermined value within a defined time period after the announcement of the warning. In one embodiment, the blood pressure of the vertebrate comprises at least one of a systolic blood pressure and a diastolic blood pressure. In one embodiment, the apparatus further comprises a reporting module configured to report at least one of the systolic blood pressure and the diastolic blood pressure.

In one embodiment, the apparatus further comprises a second analysis module, the second analysis module operative in the event that the value of the secondary motion detected by the motion detector module is at least equal to the predetermined value, the second analysis module configured to analyze the signal during the deflation interval of the inflatable chamber to extract from the signal the blood pressure of the vertebrate, whereby the apparatus completes the measurement of the blood pressure of the vertebrate using the second analysis module.

In one embodiment, the deflation interval comprises at least one step deflation interval. In one embodiment, the apparatus further comprises a neonate sensor module configured to sense whether the vertebrate is a neonate vertebrate. In one embodiment, in response to a positive determination that the vertebrate is a neonate vertebrate, the apparatus completes the blood pressure measurement of the neonate vertebrate using the second analysis module. In one embodiment, the blood pressure of the neonate vertebrate comprises at least one of a systolic blood pressure and a diastolic blood pressure.

In one embodiment, the apparatus further comprises a reporting module configured to report at least one of the systolic blood pressure and the diastolic blood pressure.

In a further aspect, the invention relates to a blood pressure measurement method. The method comprises the steps of providing an inflatable chamber, the inflatable chamber operable to be inflated during an inflation interval and deflated during a deflation interval; measuring a signal comprising information indicative of a blood pressure of a vertebrate; analyzing the signal before the inflatable chamber is fully inflated to extract from the signal the blood pressure of the vertebrate; and if necessary, responsive to a control signal, analyzing the signal during the deflation interval of the inflatable chamber to extract from the signal the blood pressure of the vertebrate; whereby a measurement of the blood pressure of the vertebrate is accomplished.

In one embodiment, the deflation interval comprises at least one step deflation interval. In one embodiment, the blood pressure of the vertebrate comprises at least one of a systolic blood pressure and a diastolic blood pressure.

In one embodiment, the method further comprises reporting at least one of the systolic blood pressure and the diastolic blood pressure. In one embodiment, the method further comprises the step of sensing whether the vertebrate is a neonate vertebrate. In one embodiment, in response to a positive determination that the vertebrate is a neonate vertebrate, the method completes a blood pressure measurement of the neonate vertebrate by analyzing the signal during the deflation interval.

In one embodiment, the signal analyzed during the deflation interval comprises a signal occurring during at least one step deflation interval. In one embodiment, the blood pressure of the neonate vertebrate comprises at least one of a systolic blood pressure and a diastolic blood pressure.

In one embodiment, the method further comprises reporting at least one of the systolic blood pressure and the diastolic blood pressure.

In still another aspect, the invention features a blood pressure measurement method. The method comprises the steps of providing an inflatable chamber, the inflatable chamber operable to be inflated during an inflation interval and deflated during a deflation interval; measuring a signal comprising information indicative of a blood pressure of a vertebrate, the signal based on motion comprising information indicative of the blood pressure; analyzing the signal before the inflatable chamber is fully inflated to extract from the signal the blood pressure of the vertebrate; and detecting a secondary motion of the vertebrate distinct from the motion comprising information indicative of the blood pressure; whereby, in the event that the secondary motion is below a predetermined value, the method completes the blood pressure measurement.

In one embodiment, the blood pressure of the vertebrate comprises at least one of a systolic blood pressure and a diastolic blood pressure. In one embodiment, the method further comprises reporting at least one of the systolic blood pressure and the diastolic blood pressure. In one embodiment, the motion detection module is configured to provide a warning, the warning being generated in response to the secondary motion that exceeds the predetermined value.

In one embodiment, the method further comprises an announcement module that announces the warning. In one embodiment, the blood pressure measurement is completed if the secondary motion falls below the predetermined value within a defined time period after the announcement of the warning. In one embodiment, the blood pressure of the vertebrate comprises at least one of a systolic blood pressure and a diastolic blood pressure. In one embodiment, the method further comprises reporting at least one of the systolic blood pressure and the diastolic blood pressure.

In one embodiment, the method further comprises the steps of: in the event that the value of the secondary motion detected by the motion detector module is at least equal to the predetermined value, analyzing the signal during the deflation interval of the inflatable chamber to extract from the signal the blood pressure of the vertebrate; whereby the blood pressure of the vertebrate is determined.

In one embodiment, the deflation interval comprises at least one step deflation interval. In one embodiment, the method further comprises sensing whether the vertebrate is a neonate vertebrate. In one embodiment, in response to a positive determination that the vertebrate is a neonate vertebrate, the method determines the blood pressure of the neonate vertebrate. In one embodiment, the blood pressure of the neonate vertebrate comprises at least one of a systolic blood pressure and a diastolic blood pressure. In one embodiment, the method further comprises reporting at least one of the systolic blood pressure and the diastolic blood pressure.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

The invention provides solutions to the problem of measuring blood pressure of vertebrate patient subjects who are moving, where the motion is distinct from the motions associated with the signal comprising information indicated of the blood pressure. In one embodiment, the system detects whether the motion is significant enough and/or of long enough duration to affect the blood pressure measurement. If the motion is not too severe, and/or if the motion is of short enough duration, the blood pressure measurement is performed during an inflation interval of an inflatable chamber, such as a cuff. If the motion is sufficiently severe, and/or persists for a long enough time, a control signal is generated so that the blood pressure measurement is performed during a deflation interval of the inflatable chamber. The system can provide announcements in either or both audible or visual format. The announcements are useful to indicate that motion has been detected, and the announcements may cause the subject patient to refrain from moving. The system also includes a neonate sensor module that can detect whether the subject patient is a neonate vertebrate. An example of a neonate vertebrate is a human having an age of 28 days or less since birth. The apparatus in one or more embodiments has reporting capability, and can provide reports of systolic and/or diastolic blood pressure. In one embodiment, making the blood pressure measurement in a time interval shorter than would otherwise be required benefits a patient by reducing discomfort.

Figure 1A:
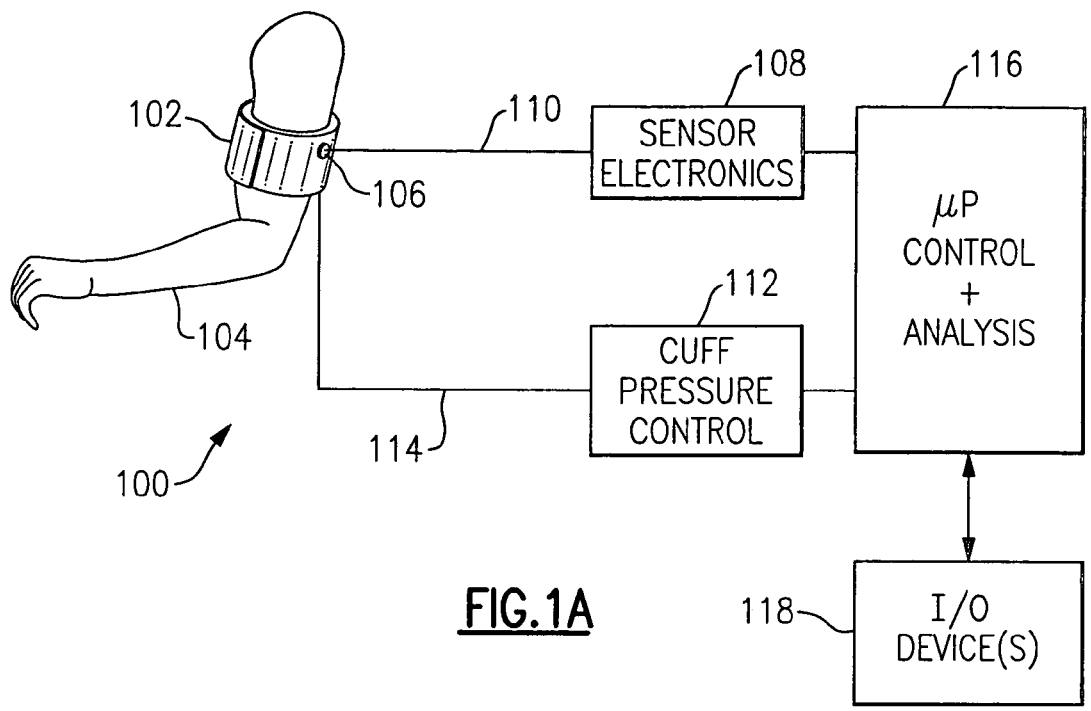
FIG. 1A illustrates in schematic overview a first system useful in making measurements of blood pressure according to principles of the invention.

FIG. 1A illustrates in schematic overview a system 100 useful in making measurements of blood pressure that embodies principles of the invention. An inflatable chamber or cuff 102 is applied to a limb 104 of a vertebrate animal. The cuff 102 has associated with it at least one sensor 106 that senses variations in pressure and/or volume within the cuff 102. The sensor 106 communicates with the sensor electronics module 108 by way of a communication link 110. In the embodiment shown, communication link 110 is depicted as a cable having one or more connections, such as a plurality of electrically conductive wires, traces on a substrate, or a fiber optic link. Alternatively, communication link 110 can be a wireless communication link such as an infrared communication channel or a wireless communication channel such as a radio channel (e.g., short range radio, WiFi, communication according to any IEEE 802.11 standard, and the like). In general communication channels described with regard to the present invention may be implemented either by communication using a cable (e.g., tethered communication connections) or by wireless methods.

In the embodiment shown, the cuff 102 is inflated during an inflation interval and deflated during a deflation interval. The inflation and deflation of the cuff 102 is controlled by a cuff pressure control module 112 that inflates and deflates the cuff 102 by way of an inflation/deflation tube 114 that provides a pressurizing fluid (such as pressurized air) to the cuff 102. A pump, a compressor, or another supply of pressurized fluid is provided, but is not shown in FIG. 1A. The inflation and deflation rate and timing of the cuff 102 is controlled by the cuff pressure control module 112 using valves or other known devices for controlling flows and pressures of pressurized fluids through the tube 114. In various embodiments, the tube 114 is either a single lumen tube or a dual lumen tube. Overall control of the operation of both the sensor electronics module 108 and the cuff pressure control module 112 is exercised by a microprocessor-based control and analysis module 116 that is in electrical communication with both the sensor electronics module 108 and the cuff pressure control module 112. In some embodiments, modules 108, 112 and 116 are all microprocessor-based modules. In some embodiments, two or more of modules 108, 112 and 116 are combined into one module. Microprocessor-based control and analysis module 116 is also in electrical communication with an input/output (I/O) module 118. I/O module 118 can in various embodiments include any or all of a keyboard, a button, a mouse, an image scanner such as a barcode scanner, or a microphone for use by a user of the apparatus for inputting commands. I/O module 118 can in various embodiments include one or more input and output devices for loading programs into the apparatus and for communicating results of blood pressure measurements and associated information in the form of reports, such as LEDs or LED displays, communication links, disk drives, CD-ROMs, video monitors, printers, and the like. I/O module 118 can in various embodiments include enunciators for making announcements, such as warnings (e.g., indications which can be visual or auditory that a vertebrate subject being measured or tested is moving or otherwise making a secondary motion distinct from motion associated with a signal comprising information indicative of a blood pressure of a vertebrate), indication of a stage of a measurement or test (e.g., such as that a measurement or test is ready to be commenced, a measurement or test is complete, or the like), and indications of success or failure of a measurement or test or a segment of a measurement or test.

Figure 1B:
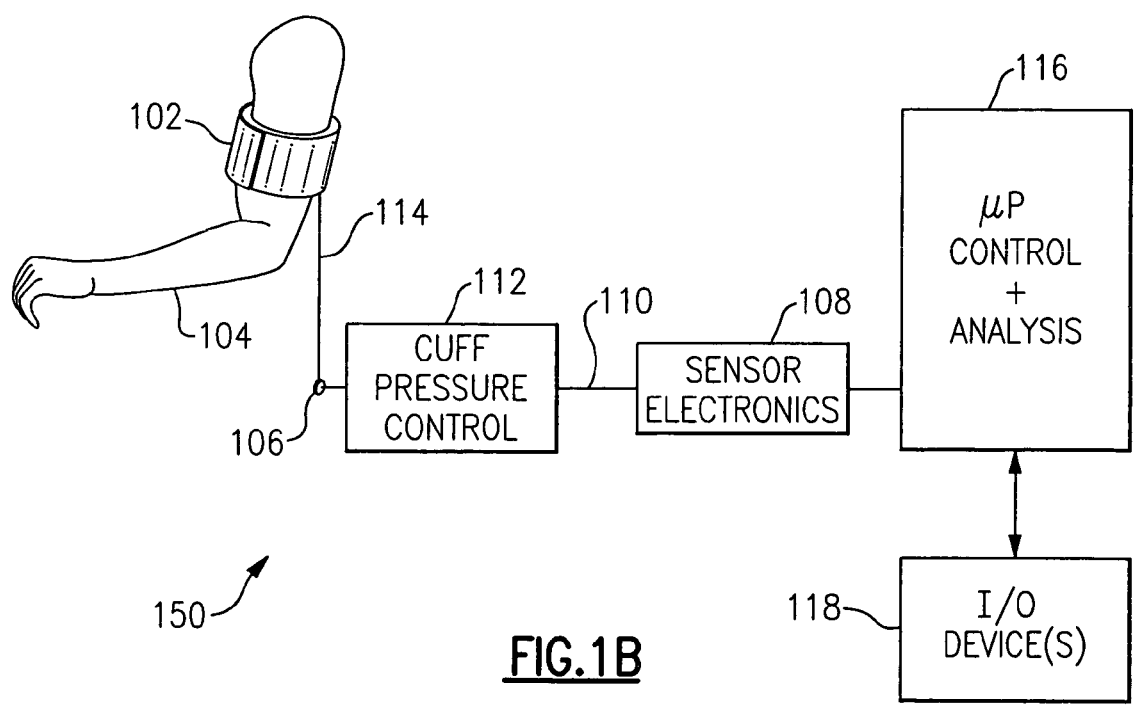
FIG. 1B illustrates in schematic overview another system useful in making measurements of blood pressure according to principles of the invention.

FIG. 1B illustrates in schematic overview another system 150 useful in making measurements of blood pressure according to principles of the invention. An inflatable chamber or cuff 102 is applied to a limb 104 of a vertebrate animal. In the embodiment shown, the cuff 102 is inflated during an inflation interval and deflated during a deflation interval. The inflation and deflation of the cuff 102 is controlled by a cuff pressure control module 112 that inflates and deflates the cuff 102 by way of an inflation/deflation tube 114 that provides a pressurizing fluid (such as pressurized air) to the cuff 102. A pump, a compressor, or another supply of pressurized fluid is provided, but is not shown in FIG. 1B. The inflation and deflation rate and timing of the cuff 102 is controlled by the cuff pressure control module 112 using valves or other known devices for controlling flows and pressures of pressurized fluids through the tube 114. In various embodiments, the tube 114 is either a single lumen tube or a dual lumen tube.

At least one sensor 106 that senses variations in pressure and/or volume within the cuff 102 is provided within the cuff pressure control 112 and/or the tube 114. In FIG. 1B, the sensor 106 is depicted as being within the tube 114. The sensor 106 communicates with the sensor electronics module 108 by way of a communication link 110.

Overall control of the operation of both the sensor electronics module 108 and the cuff pressure control module 112 is exercised by a microprocessor-based control and analysis module 116 that communicates with both the sensor electronics module 108 and the cuff pressure control module 112. In some embodiments, modules 108, 112 and 116 are all microprocessor-based modules. In some embodiments, two or more of modules 108, 112 and 116 are combined into one module. Microprocessor-based control and analysis module 116 is also in electrical communication with an input/output (I/O) module 118, such as is described hereinabove with regard to FIG. 1A.

Figure 2:
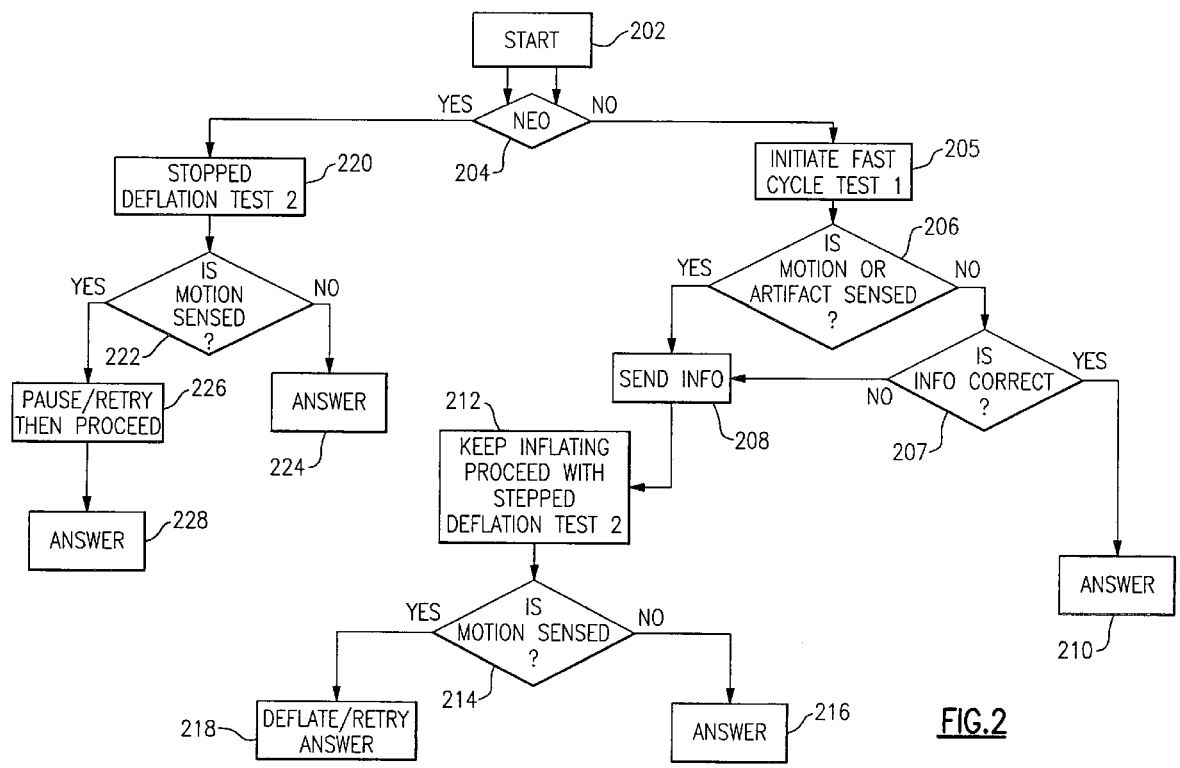
FIG. 2 is a schematic flow diagram that illustrates an exemplary embodiment of the steps in a method of measuring blood pressure, or alternatively, depicts the control logic of an apparatus useful for measuring blood pressure, according to principles of the invention.

FIG. 2 is a schematic flow diagram 200 that illustrates an exemplary embodiment of the steps in a method of measuring blood pressure, or alternatively, depicts the control logic of an apparatus useful for measuring blood pressure. As will be appreciated from FIGS. 1A and 1B described hereinbefore, each microprocessor-based module comprises both microprocessor hardware and one or more software modules that control the operation of the microprocessor-based module during a blood pressure measurement. In the present description, FIG. 2 will be described in terms of steps in a process. As will be apparent, each step can be understood as corresponding to one or more computer instructions in a software module operating on a microprocessor-based device according to principles of the invention, the computer instructions when operting controlling the steps of a blood pressure measurement performed by a microprocessor-based blood pressure measurement apparatus.

The process starts at box 202, labeled "Start," that will be understood to represent all of the steps of initiating operation of the microprocessor-based blood pressure measurement apparatus, including all necessary initial internal testing and diagnostic routines to assure proper operation of the apparatus, as well as operator entry of information needed to identify the subject vertebrate and the circumstances of the measurement. As described hereinbefore, the operator can enter information using any or all of a keyboard, a button, a mouse (in conjunction with a Graphical User Interface (GUI), a menu system, or the like), and/or audible entry of information with a microphone. As required, initialization information can also be downloaded from a database. In order to commence a measurement of the blood pressure of a vertebrate, the operator places the necessary inflatable chamber or cuff on the appropriate location of he vertebrate to be tested, such as an arm of a human being, and confirms that all of the necessary portions of the apparatus are properly made ready. The operator then issues a command to initiate the measurement, such as pressing a button. In one embodiment, at box 204, the apparatus performs an analysis of the signals that it detects to determine whether the subject vertebrate is a neonate. Alternatively, the operator can issue a command indicating that the subject is or is not a neonate.

In the event that the subject vertebrate is not a neonate, the process proceeds to box 205, at which time a "fast" cycle is initiated. The fast cycle comprises inflating the cuff 102 and sensing pressure/volume signals with sensor 106. The sensor electronic module 108 comprises a control module configured to receive as input at least a portion of the signal from the sensor 106, and to generate as output a control signal having a selected one of a plurality of values responsive to said input. As indicated by box 206, a determination is made as regards the extent of motion (or other artifacts) distinct from the expected signal indicative of a blood pressure measurement. A motion detection module configured to receive as input at least a portion of the signal from the sensor performs the determination. Depending at least in part on the magnitude of the control signal, the blood pressure signal is deemed to be suitable for analysis or unsuitable. The signals so sensed are analyzed using a first analysis module. As indicated by box 207, the analyzed information is evaluated to determine of the answer appears to be correct. If the answer appears to be correct, and the blood pressure measurement so arrive at is deemed appropriate, an "answer" or result is obtained, and in some embodiments is enunciated at box 210. The enunciated result can be any one or more of a specific value of systolic and/or diastolic blood pressure, an indication of "low," "normal," or "high" blood pressure, an indication of a good reading, and an indication that the measurement might be suspect and perhaps should be repeated, for example if an arrhythmia is detected.

As used herein, the term "predetermined value" means a value set prior to making a blood pressure measurement. Prior to beginning the measurement, the value can be adjusted. In some embodiments, the value can be a value corresponding to a default value, a value selected based on a known attribute or condition of a patient, such as age, medical condition, or prior medical history, or a value set by an operator of the apparatus using an input to the apparatus. The predetermined value can include at least one of an amplitude and a duration.

In the event that the control signal indicates some secondary motion or other artifact, the process can include a step wherein a warning is given. In different embodiments, the warning is enunciated visually or audibly. The warning in some embodiments is made known to the operator only, and in other embodiments the warning is made known to both the operator and to the subject vertebrate. If the secondary motion or artifact is of small enough magnitude and/or of short enough duration (e.g., below a predetermined value), for example where the subject vertebrate responds to the warning or to the operator by ceasing the secondary motion, the process continues with the steps corresponding to boxes 207 and 210.

In the event that the control signal indicates that the secondary motion or artifact is of sufficiently large magnitude and/or of long enough duration, for example where the subject vertebrate fails to respond to the warning or to the operator by ceasing the secondary motion, the process continues with the steps corresponding to boxes 208, 212, 214, 216 and 218 as necessary. In some embodiments, as indicated by box 208, the information obtained during the inflation cycle of box 205 is saved for further use. Alternatively, the process can optionally omit saving information, and can proceed through box 208 without saving information. In some embodiments, as indicated at box 212, when the secondary motion or artifact is sufficient to make the measurement inaccurate, the process completes the inflation portion of an inflation/deflation cycle so that sufficient pressure is applied to perform a blood pressure measurement during a deflation interval. As further indicated by box 212, the measurement of blood pressure during a deflation interval is performed, including the use of at least one step deflation interval. As indicated at box 214, a further analysis using a second analysis module is performed to extract a blood pressure measurement from the signal. If secondary motion and/or other artifacts that would disrupt the measurement are absent or are below a predetermined value, the answer or result is provided as indicated at box 216. If the secondary motion/artifact is too large, the inflatable chamber or cuff 102 is deflated and as necessary a second measuring cycle is attempted, beginning at box 205 again.

In some embodiments, if it is discovered at box 207 that the answer is not correct, the information obtained during an inflation cycle is retained. The information obtained during the inflation cycle is available for recording as part of a subject's record as necessary, and is available for analysis and/or comparison with information obtained during the deflation cycle. In the event that ther information obtained is deemed incorrect as indicated by the arrow labeled "No" leaving box 207, the process continues as represented by boxes 208, 212, 214, 216 and 218, which have been described hereinbefore.

If the device senses, or if the operator indicates, that the subject vertebrate is a neonate, the process advances from box 204 to box 220. The process in one embodiment as described in box 220 proceeds directly to a stepped deflation test. The process inflates the inflatable chamber or cuff 102 so that sufficient pressure is applied to perform a blood pressure measurement during a deflation interval. As further indicated by box 220, the measurement of blood pressure during a deflation interval is performed, including the use of at least one step deflation interval. As indicated at box 222, a further analysis using a second analysis module is performed to extract a blood pressure measurement from the signal. If secondary motion and/or other artifacts that would disrupt the measurement are absent or are below a predetermined value, the answer or result is provided as indicated at box 224. If the secondary motion/artifact is too large, the inflatable chamber or cuff 102 is deflated and as necessary a second measuring cycle is attempted, as indicated at box 226. If a successful outcome is obtained, an answer or result is provided, as indicated at box 228.

Those of ordinary skill will recognize that many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

While the present invention has been explained with reference to the structure disclosed herein, it is not confined to the details set forth and this invention is intended to cover any modifications and changes as may come within the scope of the following claims.

What is claimed is:

1. A blood pressure measurement apparatus configured to operate according to an oscillometric method of measuring blood pressure, comprising:
    an inflatable chamber, said inflatable chamber operable to be inflated during an inflation interval and deflated during a deflation interval;
    a sensor coupled to said inflatable chamber, said sensor configured to measure a signal according to the oscillometric method of measuring blood pressure, said signal comprising information indicative of a blood pressure of vertebrate;
    a control module configured to receive as input at least a portion of said signal from said sensor, and to generate as output a control signal having a selected one of a plurality of values responsive to said input;
    a first analysis module, said first analysis module configured to analyze said signal during said inflation interval of said inflatable chamber at a rate greater than 3 mmHg per second before said inflatable chamber is fully inflated to extract from said signal a systolic blood pressure and a diastolic blood pressure of said vertebrate according to the oscillometric method of measuring blood pressure;
    a second analysis module, said second analysis module selectively operative in response to one of said plurality of values of said control signal, said second analysis module configured to analyze said signal during said deflation interval of said inflatable chamber to extract from said signal said blood pressure of said vertebrate according to the oscillometric method of measuring blood pressure; and
    a neonate sensor module configured to represent whether said vertebrate is a neonate vertebrate;
    wherein in response to a positive determination that said vertebrate is a neonate vertebrate, said apparatus completes a blood pressure measurement of said neonate vertebrate using said second analysis module.

2. The apparatus of claim 1, wherein said signal analyzed by said second analysis module during said deflation interval comprises a signal occurring during at least one step deflation interval.

3. The apparatus of claim 1, wherein said blood pressure of said neonate vertebrate comprises at least one of a systolic blood pressure and a diastolic blood pressure.

4. The apparatus of claim 3, further comprising a reporting module configured to report at least one of said systolic blood pressure and said diastolic blood pressure.

5. The apparatus of claim 1, wherein said neonate sensor module configured to represent whether said vertebrate is a neonate vertebrate comprises a neonate sensor module configured to deduce from a command issued by an operator whether said vertebrate is a neonate vertebrate.

6. The apparatus of claim 1, wherein said neonate sensor module configured to represent whether said vertebrate is a neonate vertebrate comprises a neonate sensor module configured to deduce from data in a database whether said vertebrate is a neonate vertebrate.

7. A blood pressure measurement apparatus configured to operate according to an oscillometric method of measuring blood pressure, comprising:
    an inflatable chamber, said inflatable chamber operable to be inflated during an inflation interval and deflated during a deflation interval;
    a sensor coupled to said inflatable chamber, said sensor configured to measure a signal according to the oscillometric method of measuring blood pressure, said signal comprising information indicative of a blood pressure of a vertebrate;

a control module configured to receive as input at least a portion of said signal from said sensor, and to generate as output a control signal having a selected one of a plurality of values responsive to said input;

a first analysis module, said first analysis module configured to analyze said signal during said inflation interval of said inflatable chamber at a rate greater than 3 mmHg per second before said inflatable chamber is fully inflated to extract from said signal a systolic blood pressure and a diastolic blood pressure of said vertebrate according to the oscillometric method of measuring blood pressure;

a second analysis module, said second analysis module selectively operative in response to one of said plurality of values of said control signal, said second analysis module configured to analyze said signal during said deflation interval of said inflatable chamber to extract from said signal said blood pressure of said vertebrate according to the oscillometric method of measuring blood pressure;

a motion detection module configured to receive as input at least a portion of said signal from said sensor, said motion detection module configured to detect a secondary motion of said vertebrate distinct from motion associated with said signal comprising information indicative of a blood pressure of a vertebrate and configured to communicate a value to said first analysis module; and a neonate sensor module configured to represent whether said vertebrate is a neonate vertebrate;

whereby, in the event that said value of said secondary motion detected by said detection module is below a predetermined value, said apparatus completes a blood pressure measurement of said vertebrate using said first analysis module; and wherein in response to a positive determination that said vertebrate is a neonate vertebrate, said apparatus completes said blood pressure measurement of said neonate vertebrate using said second analysis module.

8. The apparatus of claim 7, wherein said neonate sensor module configured to represent whether said vertebrate is a neonate vertebrate comprises a neonate sensor module configured to deduce from a command issued by an operator whether said vertebrate is a neonate vertebrate.

9. The apparatus of claim 7, wherein said neonate sensor module configured to represent whether said vertebrate is a neonate vertebrate comprises a neonate sensor module configured to deduce from data in a database whether said vertebrate is a neonate vertebrate.

10. A blood pressure measurement apparatus configured to operate according to an oscillometric method of measuring blood pressure, comprising:

an inflatable chamber, said inflatable chamber operable to be inflated during an inflation interval and deflated during a deflation interval;

a sensor coupled to said inflatable chamber, said sensor configured to measure a signal according to the oscillometric method of measuring blood pressure, said signal comprising information indicative of a blood pressure of a vertebrate;

a control module configured to receive as input at least a portion of said signal from said sensor, and to generate as output a control signal having a selected one of a plurality of values responsive to said input;

a first analysis module, said first analysis module configured to analyze said signal during said inflation interval of said inflatable chamber at a rate greater than 3 mmHg per second before said inflatable chamber is fully inflated to extract from said signal a systolic blood pressure and a diastolic blood pressure of said vertebrate according to the oscillometric method of measuring blood pressure;

a second analysis module, said second analysis module selectively operative in response to one of said plurality of values of said control signal, said second analysis module configured to analyze said signal during said deflation interval of said inflatable chamber to extract from said signal said blood pressure of said vertebrate according to the oscillometric method of measuring blood pressure;

a motion detection module configured to receive as input at least a portion of said signal from said sensor, said motion detection module configured to detect a secondary motion of said vertebrate distinct from motion associated with said signal comprising information indicative of a blood pressure of a vertebrate and configured to communicate a value to said first analysis module;

a neonate sensor module configured to represent whether said vertebrate is a neonate vertebrate; and a reporting module configured to report at least one of said systolic blood pressure and said diastolic blood pressure;

whereby said apparatus completes said measurement of said blood pressure of said vertebrate using at least one of said first analysis module and said second analysis module; and whereby, in the event that said value of said secondary motion detected by said detection module is below a predetermined value, said apparatus completes a blood pressure measurement of said vertebrate using said first analysis module.

11. An oscillometric blood pressure measurement method, comprising the steps of:

providing an inflatable chamber, said inflatable chamber operable to be inflated during inflation interval and deflated during a deflation interval;

measuring a signal comprising information indicative of a blood pressure of a vertebrate, said signal generated according to an oscillometric blood pressure measurement method;

analyzing said signal during an inflation of said inflatable chamber at a rate greater than 3 mmHg per second before said inflatable chamber is fully inflated to extract from said signal systolic blood pressure and a diastolic blood pressure of said vertebrate;

if necessary, responsive to a control signal, analyzing said signal during said deflation interval of said inflatable chamber to extract from said signal said blood pressure of said vertebrate according to an oscillometric blood pressure measurement method;

representing whether said vertebrate is a neonate vertebrate;

wherein in response to a positive determination that said vertebrate is a neonate vertebrate, said method completes a blood pressure measurement of said neonate vertebrate by analyzing said signal during said deflation interval, whereby a measurement of said blood pressure of said vertebrate according to an oscillometric blood pressure measurement method is accomplished.

12. The method of claim 11, wherein said signal analyzed during said deflation interval comprises a signal occurring during at least one step deflation interval.

13. The method of claim 11, further comprising reporting at least one of said systolic blood pressure and said diastolic blood pressure.

14. An oscillometric blood pressure measurement method, comprising the steps of:
- providing an inflatable chamber, said inflatable chamber operable to be inflated during an inflation interval and deflated during a deflation interval;
- measuring a signal comprising information indicative of a blood pressure of a vertebrate, said signal generated according to an oscillometric blood pressure measurement method;
- analyzing said signal during an inflation of said inflatable chamber at a rate greater than 3 mmHg per second before said inflatable chamber is fully inflated to extract from said signal a systolic blood pressure and a diastolic blood pressure of said vertebrate;
- if necessary, responsive to a control signal, analyzing said signal during said deflation interval of said inflatable chamber to extract from said signal said blood pressure of said vertebrate according to an oscillometric blood pressure measurement method;
- detecting a secondary motion of said vertebrate distinct from said motion comprising information indicative of said blood pressure;
- whereby, in the event that said secondary motion is below a predetermined value, said method completes said blood pressure measurement; and
- in the event that said value of said secondary motion detected by said motion detector module is at least equal to said predetermined value, analyzing said signal during said deflation interval of said inflatable chamber to extract from said signal said blood pressure of said vertebrate;
- representing whether said vertebrate is a neonate vertebrate;
- wherein in response to a positive determination that said vertebrate is a neonate vertebrate, said method determines said blood pressure of said neonate vertebrate according to an oscillometric blood pressure measurement method.

15. The method of claim 14, wherein said blood pressure of said neonate vertebrate comprises at least one of a systolic blood pressure and a diastolic blood pressure.

16. The method of claim 15, further comprising reporting at least one of said systolic blood pressure and said diastolic blood pressure.

17. The method of claim 11, wherein the step of representing whether said vertebrate is a neonate vertebrate comprises the step of an operator issuing a command.

18. The method of claim 11, wherein the step of representing whether said vertebrate is a neonate vertebrate comprises the step of deducing from data in a database whether said vertebrate is a neonate vertebrate.

19. The method of claim 14, wherein the step of representing whether said vertebrate is a neonate vertebrate comprises the step of an operator issuing a command.

20. The method of claim 14, wherein the step of representing whether said vertebrate is a neonate vertebrate comprises the step of deducing from data in a database whether said vertebrate is a neonate vertebrate.

* * * * *